US00PP31803P2

(12) United States Plant Patent
Heimovaara

(10) Patent No.: US PP31,803 P2
(45) Date of Patent: May 26, 2020

(54) ***CHRYSANTHEMUM* PLANT NAMED 'ZANMUGRAPE RED'**

(50) Latin Name: ***Chrysanthemum* x *morifolium Ramat.***
Varietal Denomination: Zanmugrape Red

(71) Applicant: Van Zanten Breeding BV, Aalsmeer (NL)

(72) Inventor: Sjoukje Heimovaara, Valkenburg (NL)

(73) Assignee: Van Zanten Breeding BV (NL)

( * ) Notice: Subject to any disclaimer, the term of this patent is extended or adjusted under 35 U.S.C. 154(b) by 0 days.

(21) Appl. No.: 16/350,567

(22) Filed: Dec. 4, 2018

(51) Int. Cl.
*A01H 5/02* (2018.01)
*A01H 6/14* (2018.01)

(52) U.S. Cl.
USPC ..... Plt./293

(58) Field of Classification Search
USPC ..... Plt./263.1, 284, 286, 287, 293
See application file for complete search history.

*Primary Examiner* — Susan McCormick Ewoldt
*Assistant Examiner* — Karen M Redden
(74) *Attorney, Agent, or Firm* — Steptoe & Johnson LLP

(57) ABSTRACT

A *chrysanthemum* plant named 'Zanmugrape Red' characterized by its medium sized blooms with dark red ray florets and prolific branching; natural season flowering date October 8; blooming for a period of 5 weeks.

2 Drawing Sheets

Botanical designation: *Chrysanthemum* x *morifolium* Ramat.

Cultivar denomination: "Zanmugrape Red".

RELATED CULTIVARS

The new plant is a flower color mutant of 'Zanmugrape' (U.S. Plant Pat. No. 27,039)

BACKGROUND OF THE INVENTION

The present invention relates to a new and distinct cultivar of *chrysanthemum* plant, botanically known as *Chrysanthemum* x *morifolium* Ramat., commercially known as a garden mum, and hereinafter referred to by the cultivar denomination 'Zanmugrape Red'. 'Zanmugrape Red' is a product of a breeding and selection program which had the objective of finding flower color mutants from existing parent plants. The new plant comprises a whole plant mutant of the parent *chrysanthemum* named 'Zanmugrape' (U.S. Plant Pat. No. 27,039). Plants of the new cultivar 'Zanmugrape Red' differ from plants of the female parent in the color of the ray-florets. The ray-florets of the parent are purple, while those of the new plant are dark red.

In order to obtain color mutants, unrooted cuttings of the parent plant were irradiated in January 2015 at Ziekenhuis, Rotterdam, the Netherlands, with gamma radiation at a dose of 15 Gy. These treated cuttings were then planted in a controlled environment (greenhouse) in Rijsenhout, the Netherlands. In this population of planted cuttings, the new cultivar was discovered as a natural flower color mutant in March 2016 by Sjoukje Heimovaara. The first act of asexual reproduction of 'Zanmugrape Red' was accomplished when after planting of the mutant as a motherplant in April 2016, vegetative cuttings from this motherplant were taken and propagated further in Rijsenhout, the Netherlands. In summer, about 6-8 days are needed to initiate roots in cuttings of the new cultivar, after another 5 days rooted plants are formed. The new cultivar has been found to retain its distinctive characteristics through successive propagations.

BRIEF DESCRIPTION OF THE DRAWINGS

The present invention of a new and distinct variety of *chrysanthemum* (of about 22 weeks) is shown in the accompanying drawings, the color being as nearly true as possible with color photographs of this type.

DESCRIPTION OF THE INVENTION

Figure 1:
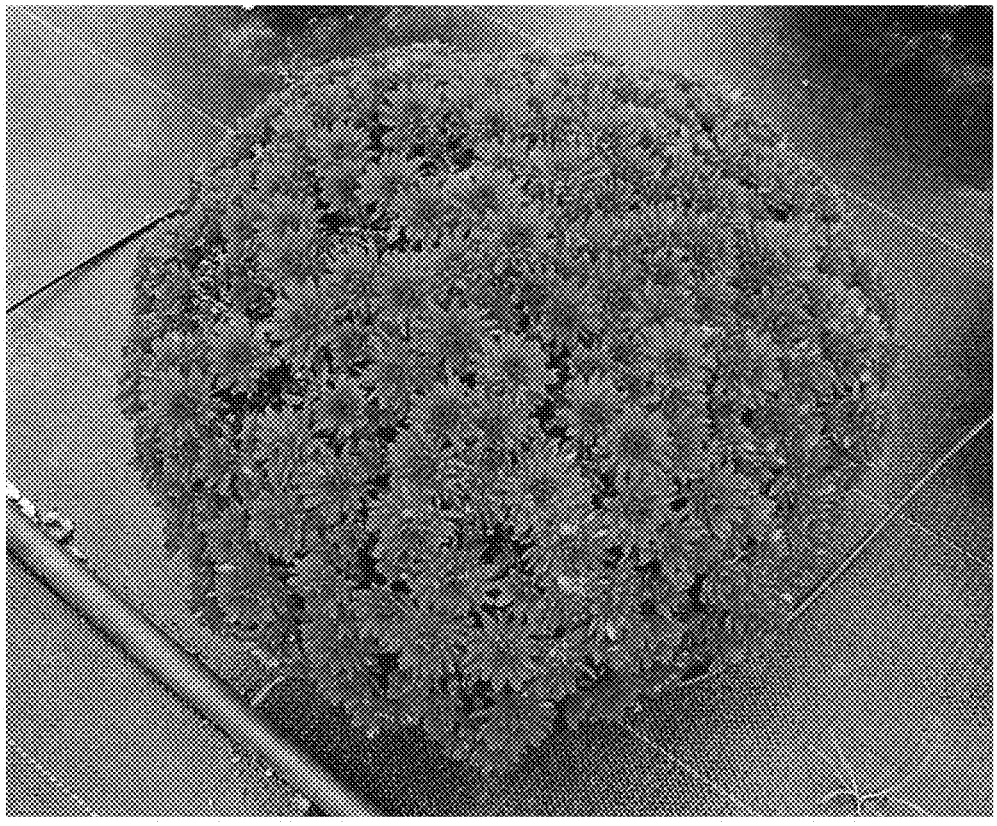
FIG. 1 shows a plant of the new cultivar in full bloom.
Figure 2:
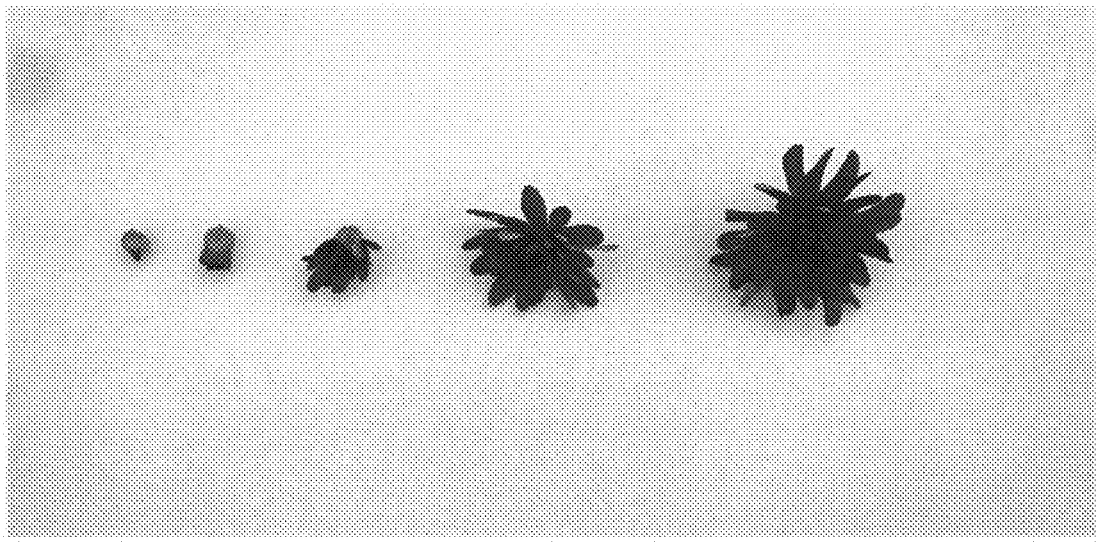
FIG. 2 shows the various stages of blooms of the new cultivar.
Figure 3:
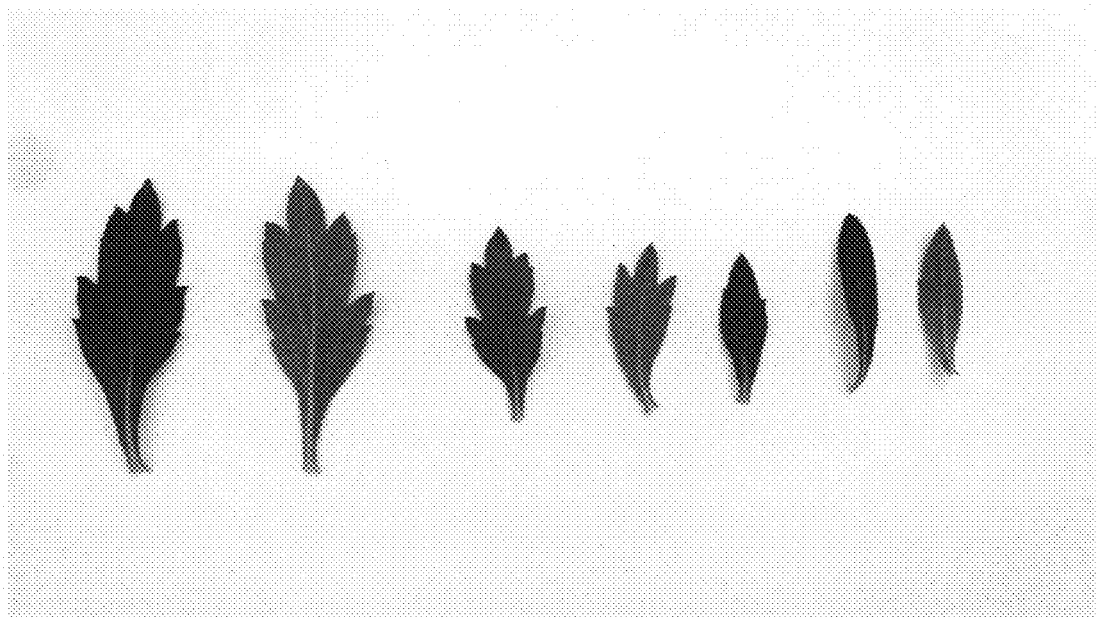
FIG. 3 shows the various stages of foliage of the new cultivar.

The observations and measurements were gathered from plants in the period of 19 to 26 weeks of age grown outdoor in Rijsenhout, the Netherlands, under natural day length and temperature and planted in week 21 in 2018. The natural blooming date of this crop was October 8 (week 41). The average height of the plants was 28 cm. No growth retardants were used. No tests were done on disease or insect resistance or susceptibility. No tests were done on cold or drought resistance. This new variety produces medium sized blooms with dark red ray florets blooming for a period of five weeks.

From the cultivars known to the inventor the most similar existing cultivar in comparison to 'Zanmugrape Red' is 'Zanmugrape' (U.S. Plant Pat. No. 27,039). When 'Zanmugrape' and 'Zanmugrape Red' are compared the following difference is noticed: Ray florets of 'Zanmugrape' are red-purple and those of 'Zanmugrape Red' are more dark red.

The following is a description of the plant and characteristics that distinguish 'Zanmugrape Red' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, sixth edition (2005).

Botanical Description of *Chrysanthemum* x *morifolium* Ramat. 'Zanmugrape Red'

Bud:
- *Size*.—Small; cross-section 3 mm, height 3 mm.
- *Shape*.—Round.
- *Texture*.—Pubescent.
- *Outside color*.—Greyed-green 191A.

Phyllaries:
- *Number*.—24, arranged in 3 rows.
- *Shape*.—Elliptic.
- *Apex*.—Acute.
- *Base*.—Truncate.
- *Margin*.—Entire.
- *Color*.—Upper side: Yellow-green 144A. Lower side: Greyed-green 191C.
- *Length and width*.—3 mm; 1.5 mm.
- *Texture*.—Pubescent.

Inflorescences:
- *Type*.—Double.
- *Height*.—1 cm.
- *Diameter*.—4.5 cm.
- *Peduncle length*.—5-7.5 cm.
- *Peduncle color*.—Green 138C.
- *Peduncle diameter*.—1.5 mm.
- *Peduncle texture*.—Pubescent.
- *Peduncle strength*.—Strong.
- *Number per branch*.—About 6-7 inflorescences.
- *Duration of flowering*.—5 weeks.
- *Seeds*.—Produced in small quantities, ovate, Greyed-brown 199A, length 1.5 mm, diameter 0.5 mm; texture: rough with ribs.
- *Fragrance*.—Faint *chrysanthemum* odor.

Color inflorescences:
- *Center of inflorescence*.—Immature stage: Dark red 187B; Mature stage: Dark red 187B.
- *Color of upper side of ray florets*.—Dark red 187B to 187C.
- *Color of lower side of ray florets*.—Dark red 186 B.
- *Tonality from distance*.—A garden mum with dark red blooms.
- *Color of ray florets after aging of the plant*.—Dark red 185B.

Ray florets:
- *Number of types*.—One.
- *Type*.—Ligulate.
- *Texture*.—Upper and lower side smooth.
- *Number*.—100-110.
- *Shape*.—Elliptic.
- *Apex*.—Dentate.
- *Base*.—Attenuate.
- *Cross-section*.—Flat.
- *Longitudinal axis*.—Straight.
- *Length of corolla tube*.—3 mm.
- *Diameter corolla tube*.—1 mm.
- *Ray floret margin*.—Entire.
- *Ray floret length*.—1-2.5 cm.
- *Ray-floret width*.—2-4 mm.
- *Ratio length/width*.—High.

Disc florets: Absent.

Receptacle:
- *Color*.—Yellow-green 145D.
- *Shape*.—Domed raised.
- *Height*.—3.5-4 mm.
- *Diameter*.—3 mm.

Reproductive organs:
- *Androecium*.—Absent.
- *Gynoecium*.—Present on ray florets.
- *Style color*.—Yellow-green 154C.
- *Style length*.—4 mm.
- *Stigma color*.—Yellow 7A.
- *Stigma width*.—1 mm.
- *Ovary*.—Enclosed in calyx.
- *Ovary color*.—Yellow-green 149D.

Plant:
- *Type*.—Bushy.
- *Growth habit*.—Spherical shape.
- *Growth rate*.—Medium to high.
- *Height*.—25-28 cm.
- *Width*.—45 cm.
- *Stem color*.—Greyed-brown 199A.
- *Stem strength*.—Medium.
- *Stem brittleness*.—Brittle.
- *Stem anthocyanin coloration*.—Present.
- *Internode length*.—1-2 cm.
- *Length of lateral branch*.—From top to bottom 17-19 cm.
- *Lateral branch color*.—Green 138 C.
- *Lateral branch, attachment*.—Strong.
- *Lateral branch diameter*.—2.mm.
- *Lateral branch texture*.—Pubescent with ribs.
- *Branching* (*average number of lateral branches*).—Prolific with 7 breaks after pinching.
- *Natural season blooming date*.—October 8 (week 41) in Rijsenhout, the Netherlands.
- *Root habits*.—Fine, freely branching.
- *Root color*.—White 155D.
- *Rooting time*.—6-8 days.
- *Formation rooted plants*.—12-14 days.

Foliage:
- *Leaf glossiness*.—Upper side: very weak. Lower side: very weak.
- *Leaf color*.—Upper side: Green 137A. Lower side: Green 137C.
- *Color midvein*.—Upper side: Yellow-green 147D. Lower side: Yellow-green 148D.
- *Size*.—Small; length 2.8-5 cm, width 0.8-2 cm.
- *Quantity* (*number per lateral branches*).—16-18.
- *Shape*.—Elliptic.
- *Texture upper side*.—Sparsely pubescent.
- *Texture under side*.—Pubescent.
- *Venation arrangement*.—Pinnate.

*Shape of margin*.—Serrated to entire.
*Shape of base of sinus between lateral lobes*.—Rounded.
*Margin of sinus between lateral lobes*.—Diverging.
*Shape of base*.—Truncate to asymmetric.
*Apex*.—Mucronulate.
*Petiole attitude*.—Moderately upwards.
*Petiole length*.—0.5-1 cm.
*Petiole diameter*.—1.5 mm.
*Petiole color*.—Yellow-green 147D.
*Stipules*.—Small.

Differences with the comparison variety, when grown under identical conditions

| | 'Zanmugrape Red' | 'Zanmugrape' |
|---|---|---|
| Ray-floret color | Dark red 187B to 187C | Red-purple 61A |

I claim:

1. A new and distinct *chrysanthemum* plant named 'Zanmugrape Red' as described and illustrated.

* * * * *